United States Patent [19]
Dubief et al.

[11] Patent Number: 6,074,633
[45] Date of Patent: Jun. 13, 2000

[54] DETERGENT COSMETIC COMPOSITION CONTAINING AN OXYALKYLENATED SILICONE

[75] Inventors: Claude Dubief, Le Chesnay; Danièle Cauwet-Martin, Paris, both of France

[73] Assignee: L'Oreal, Paris, France

[21] Appl. No.: 08/825,712

[22] Filed: Mar. 19, 1997

[30] Foreign Application Priority Data

Mar. 21, 1996 [FR] France .................................. 96 03543
Feb. 7, 1997 [EP] European Pat. Off. .............. 97400284

[51] Int. Cl.$^7$ ................................ A61K 7/06; A61K 7/00
[52] U.S. Cl. .................................... 424/70.19; 424/70.21; 424/401; 424/70.22; 424/70.31; 424/70.12; 510/119; 510/129; 514/881
[58] Field of Search .............................. 424/70.12, 70.19, 424/70.21, 401, 70.22, 70.31; 510/119, 129; 514/881

[56] References Cited

U.S. PATENT DOCUMENTS 5,217,652  6/1993  Iovanni .................................. 252/547
5,556,628  9/1996  Derian et al. ........................... 424/401

FOREIGN PATENT DOCUMENTS 0155806  9/1985  European Pat. Off. .
0521748  1/1993  European Pat. Off. .
0613942  9/1994  European Pat. Off. .
0633018  1/1995  European Pat. Off. .
2694494  2/1994  France .

OTHER PUBLICATIONS

Harry's Cosmeticology 7$^{th}$ Ed.: Chap. 12: Shaving Preparations, Chemical Publishing, New York, pp. 156–163 (1982).

H.P. Fiedler, Lexikon der Hilfsstoffe für Pharmazie, Kosmetik und angrenzende Gebiete, Editio Cantor, Aulendorf, p. 382 (1989).

Chemie Lexikon, Georg Thieme Verlag, Stuttgart, pp. 1121–1123 (1990).

Josef ROIDL, "Anwendung von Siliconpolymeren und Silicone mit funktionellen Gruppen in der Kosmetik", Seifen–Ole–Fette–Wasche, 112 (4) : 123–126 (1986).

English Derwent Abstract of EP–A–0521748, Jul. 1993.
English Derwent Abstract of EP–A–0633018, Jun. 1994.

*Primary Examiner*—Thurman K. Page
*Assistant Examiner*—Brian K. Seidleck
*Attorney, Agent, or Firm*—Finnegan, Henderson, Farabow, Garrett & Dunner, L.L.P.

[57] ABSTRACT

A cosmetic composition containing at least one anionic detergent surfactant, at least one nonionic or amphoteric cosurfactant, at least one electrolyte and at least one oxyalkylenated silicone, and a process for cleaning and/or washing the skin or keratin fibers comprising applying a cosmetic composition as defined above and rinsing with water.

32 Claims, No Drawings

DETERGENT COSMETIC COMPOSITION CONTAINING AN OXYALKYLENATED SILICONE

The present invention relates to new cosmetic compositions intended for cleaning the hair, the scalp and/or the skin containing at least one detergent (anionic) surfactant, at least one nonionic or amphoteric cosurfactant, at least one electrolyte and at least one oxyalkylenated silicone, and to the use of these compositions in cosmetic applications.

The use of detergent cosmetic compositions, i.e., shampoos or shower gels, containing surface-active agents with a washing power and one or a number of conditioners is commonplace for cleaning the hair and/or the skin.

In order to improve the cosmetic properties of detergent compositions, and more particularly those which are intended to be applied on sensitized hair, i.e., hair which has been damaged or embrittled, in particular by the chemical action of atmospheric agents and/or hair treatments, such as permanent waves, dyeing or bleaching, it is often necessary to introduce additional cosmetic conditioning agents into these compositions, such as, for example, silicones, which provide the treated hair with ease of disentangling and of styling, as well as markedly increased softness and sheen.

Likewise, it may be advantageous to treat the scalp with compositions containing active principles, such as antidandruff agents.

Given the insoluble nature of most conditioning agents and of some antidandruff agents in the aqueous media used in shampoos, the agents are generally maintained in dispersed form. This dispersed form allows the conditioning agents or antidandruff agents to be deposited on the hair or on the skin and not to be entirely removed during rinsing. It is important, however, that the suspended form does not disturb the detergent and foaming properties of the cosmetic composition.

Because this is a difficult problem to solve, few means exist to date for efficiently keeping insoluble agents in suspension. To this end the use of long-chain ester or ether derivatives or polysaccharides such as xanthan gum have already been proposed. However, long-chain esters or ethers exhibit crystallization problems which bring about a change, i.e., an increase in the viscosity of the compositions over time. Gelling polysaccharides also exhibit drawbacks, namely, it is difficult to develop a foam with detergent compositions containing them, i.e., poor commencement of foaming, and the compositions do not have a smooth texture and flow in blobs, which is not appreciated by users.

French Patent Application 2,694,494 discloses compositions containing, in suspension, water-insoluble particles containing an anionic surfactant, a non-ionic or amphoteric cosurfactant and an electrolyte. The surfactants are present in an amount such that the compositions have a pseudo plastic behavior with a yield point greater than 0.2 Pa and exhibit a lamellar phase structure enclosing spherulites capable of maintaining water-insoluble particles in suspension.

However, these compositions, which allow particles to be placed in suspension, exhibit properties upon use which are not satisfactory, especially when used as a shampoo or shower gel. In particular, the foaming properties, such as commencement of foaming, are not completely satisfactory. The foams are generally too dense and difficult to work.

Applicants have thus sought to improve the foaming properties of these compositions.

An object of the present invention is thus detergent cosmetic compositions possessing good foaming properties which are capable of keeping water-insoluble active principles in suspension.

Applicants have now found that this objective is achieved by introducing an oxyalkylenated silicone into a mixture comprising at least one anionic surfactant, at least one non-ionic or amphoteric cosurfactant and at least one electrolyte, wherein the compounds are present in amounts effective to provide the composition with the following:

(a) rheological flow behavior characterized by a range of stresses for which the viscosity is constant, followed by a range of stresses for which the viscosity decreases as the stress increases, and (b) a lamellar phase structure capable of maintaining in suspension water-insoluble particles optionally present in the composition.

The foaming properties of the compositions, such as commencement, copiousness and behavior of the foam, are markedly improved.

The compositions according to the invention are stable, making it possible to keep water-insoluble liquid or solid particles in suspension.

A subject of the invention is thus a detergent cosmetic composition, comprising at least one anionic surfactant, at least one non-ionic or amphoteric cosurfactant, at least one oxyalklenated silicone and at least one electrolyte, wherein the compounds are present in amounts effective to provide the composition with the following:

(a) rheological flow behavior characterized by a range of stresses for which the viscosity is constant, followed by a range of stresses for which the viscosity decreases as the stress increases, and (b) a lamellar phase structure capable of maintaining in suspension water-insoluble particles optionally present in the composition.

Moreover, the composition exhibits good washing properties and advantageous cosmetic properties, i.e., softness, disentangling and styling.

The rheological flow behavior of the compositions is characterized using a controlled-stress rheometer (Carrimed CSHR100). The measurements are carried out at 25° C. using a cone-plate measuring body with an angle of 2 degrees and a diameter of 6 cm.

The stresses for which the viscosity of a given composition is constant are variable. Preferably, according to the present invention, they range from 0.001 to 10 Pa and more preferably they range from 0.01 to 2 Pa.

The compositions according to the invention exhibit a lamellar phase, that is to say a hydrated solid or liquid crystal phase in which a number of bilayers are arranged in a parallel network, separated by layers of water or of aqueous solution.

The lamellar phase can optionally contain spherulites which are polylamellar vesicles composed of a number of layers of surfactants arranged concentrically and with sizes generally ranging from 0.1 to 50 micrometres.

Another subject of the invention is a process for cleaning the hair, the skin and/or the scalp using the above described compositions.

Mention may preferably be made, as examples of anionic surfactants which can be used, alone or as a mixture, in the context of the present invention, of salts, in particular alkali metal salts, especially sodium salts, ammonium salts, amine salts, amino alcohol salts or magnesium salts, of the following compounds: alkyl sulphates, alkyl ether sulphates, alkylamido ether sulphates, monoglyceride sulphates, alkyl glyceryl sulphonates, alkyl sulphonates, alkyl phosphates, alkyl amide sulphonates, alkylaryl sulphonates, α-olefin sulphonates, alkyl sulphosuccinates, alkyl ether sulphosuccinates, alkyl amide sulphosuccinates, alkyl sulphosuccinamates, alkyl sulphoacetates, alkyl ether phosphates, acylisethionates or N-acylamino acids, such as N-acylsarcosinates, N-acylglutamates and N-acyltaurates. Mention may also be made of salts of fatty acids, such as the salts of undecylenic, oleic, ricinoleic, palmitic or stearic acids, coconut oil acid or hydrogenated coconut oil acid; or acyl hydroxy acids, such as acyllactylates. Weakly anionic surfactants may also be used, such as alkyl D-galactosiduronic acids and their salts, as well as polyoxy-alkylenated ether carboxylic acids, in particular those containing from 2 to 24 ethylene oxide groups, and their mixtures. The alkyl or acyl radical of all these various compounds preferably contains from 8 to 22 carbon atoms.

Mention may preferably be made, as non-ionic cosurfactants which can be used according to the invention, of ethoxylated, propoxylated or glycerolated fatty acids, alkyl phenols, α-diols or alcohols, each having a fatty chain containing from 8 to 28 carbon atoms, it being possible for the number of ethylene or propylene oxide groups to range from 1 to 50 and that of glycerol groups to range in particular from 1 to 30. Mention may also preferably be made of copolymers of ethylene oxide and of propylene oxide, condensates of ethylene oxide and of propylene oxide with fatty alcohols, polyethoxylated fatty amides or amines preferably having from 2 to 30 mol of ethylene oxide, polyglycerolated fatty amides containing on average from 1 to 5 glycerol groups, polyglycerolated diglycolamides, optionally oxyethylenated fatty acid esters of sorbitan, fatty acid esters of sucrose, polyoxyalkylenated fatty acid esters, optionally oxyalkylenated alkylpolyglycosides, alkyl glucoside esters, N-alkylglucamine and N-acylmethylglucamine derivatives, amine oxides and their mixtures.

Mention may preferably be made, as amphoteric cosurfactants which can be used according to the invention, of secondary or tertiary aliphatic amine derivatives in which the aliphatic radical is a linear or branched chain containing from 8 to 22 carbon atoms and containing at least one water-solubilizing anionic group, for example, carboxylate, sulphonate, sulphate, phosphate or phosphorate. Mention may more preferably be made of alkyl betaines, alkyl dimethyl betaines, alkyl sulphobetaines, alkylamidoalkyl betaines, alkylamidoalkyl sulphobetaines, imidazoline derivatives, such as amphocarboxyglycinate or amphocarboxypropionate derivatives, and their mixtures.

The preferred cosurfactants according to the invention are selected from alkyl betaines and alkylamidoalkyl betaines.

The anionic surfactant or surfactants are preferably present in the compositions in according to the invention in amounts ranging from 3 to 50% by weight, and more preferably from 5 to 30% by weight, with respect to the total weight of the composition.

The at least one cosurfactant is preferably present in the compositions according to the invention in amounts ranging from 0.05 to 30% by weight, and more preferably ranging from 1 to 15% by weight, with respect to the total weight of the composition.

The sum of the concentrations of anionic surfactants and of cosurfactants preferably ranges from 3 to 70% by weight with respect to the total weight of the composition.

The cosurfactant/anionic surfactant ratio by weight is preferably less than or equal to 1, and more preferably ranges from 0.01 to 1, and still more preferably ranges from 0.05 to 0.75.

Mention may preferably be made, among the electrolytes, of metal salts or salts of amines, of ammonium or of basic amino acids.

The metal salts are preferably selected from alkali metal salts, alkaline-earth metal salts, transition metal salts and salts of metals from groups 111A and IVA of the Periodic Classification of the Elements.

Mention may preferably be made, as alkali metal salts which are useful according to the invention, of lithium, sodium and potassium salts.

Mention may preferably be made, as alkaline-earth metal salts which are useful according to the invention, of beryllium, magnesium, calcium, strontium and/or barium salts.

Mention may preferably be made, as transition metal salts which are useful according to the invention, of lanthanide salts and salts of metals from the fourth period of the Periodic Classification of the Elements, such as manganese, cobalt and zinc salts.

Mention may preferably be made, as salts of metals from groups IIIA and IVA of the Periodic Classification of the Elements which are useful according to the invention, of aluminium and tin salts.

In the context of the present invention the term "lanthanide" is understood to mean elements with an atomic number ranging from 57 to 71, i.e., lanthanum, cerium, praseodymium, neodymium, promethium, samarium, europium, gadolinium, terbium, dysprosium, holmium, erbium, thulium, ytterbium and lutetium.

The metal salts according to the invention are preferably selected from lithium, strontium, barium, yttrium, neodymium, gadolinium, manganese and zinc salts, more preferably from strontium salts.

These salts can be, for example, carbonates, bicarbonates, sulphates, glycerophosphates, borates, chlorides, nitrates, acetates, hydroxides or persulphates, as well as salts of α-hydroxy acids or salts of fruit acids such as citrate, tartrate, lactate or malate, or alternatively salts of amino acids such as aspartate, arginate, glucocholate or fumarate, or salts of fatty acids such as palmitate, oleate, caseinate or behenate.

The salt is preferably selected from nitrates or chlorides, in particular lithium, strontium, barium, yttrium, neodymium, gadolinium, manganese or zinc nitrate or lithium, strontium, barium, yttrium, neodymium, gadolinium, manganese or zinc chloride, or sulphates or acetates, such as calcium, strontium or magnesium sulphate and strontium or magnesium acetate.

More preferably, the electrolyte is a magnesium or strontium salt which is preferably provided in the chloride or nitrate form.

According to the invention, the electrolyte concentration is preferably less than 20% by weight with respect to the total weight of the composition, more preferably ranges from 2 to 15%, and still more preferably ranges from 6 to 13%.

The oxyalkylenated silicones which can be used according to the invention can be water-soluble, spontaneously water-dispersible or water-insoluble. Preferably they are water-soluble or spontaneously water-dispersible.

The oxyalkylenated silicones are preferably selected from compounds of formulae (I), (II), (III), (IV) and (V):

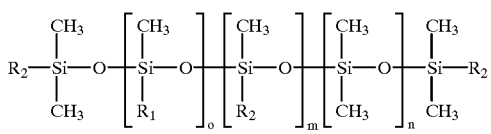
(I)

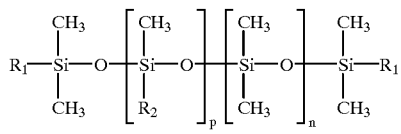
(II)

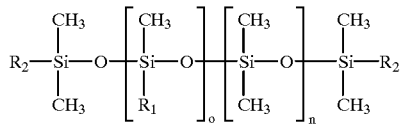
(III)

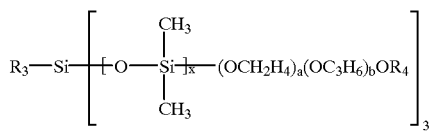
(IV)

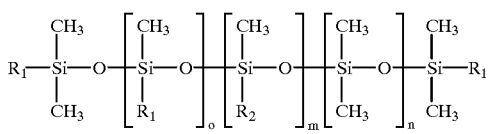
(V)

wherein:

$R_1$, which is identical or different, represents a linear or branched $C_1$–$C_{30}$ alkyl radical or a phenyl radical;

$R_2$, which is identical or different, represents —$C_cH_{2c}$—O—(—$C_2H_4O)_a$(—$C_3H_6O)_b$—$R_5$ or —$C_cH_{2c}$—O—(—$C_4H_8O)_a$—O—$R_5$;

$R_3$ and $R_4$, which are identical or different, represent a linear or branched $C_1$–$C_{12}$ alkyl radical and preferably the methyl radical;

$R_5$, which is identical or different, is a hydrogen atom; a linear or branched alkyl radical containing 1 to 12 carbon atoms; a linear or branched alkoxy radical containing 1 to 6 carbon atoms; a linear or branched acyl radical containing 2 to 12 carbon atoms; a hydroxyl radical; —$SO_3M$; —$OCOR_6$; $C_1$–$C_6$ aminoalkoxy optionally substituted on the amine, $C_2$–$C_6$ aminoacyl optionally substituted on the amine; —$NHCH_2CH_2COOM$; $N(CH_2CH_2COOM)_2$; amino alkyl optionally substituted on the amine and on the alkyl chain; $C_1$–$C_{30}$ carboxyacyl; a phosphono group optionally substituted by one or two substituted amino alkyl radicals; —$CO(CH_2)_dCOOM$; —$OCOCHR_7(CH_2)_dCOOM$; —$NHCO(CH_2)_dOH$ or —$NH_3Y$;

M, which is identical or different, represents a hydrogen atom, Na, K, Li, $NH_4$ or an organic amine;

$R_6$ represents a linear or branched $C_1$–$C_{30}$ alkyl radical;

$R_7$ represents a hydrogen atom or an $SO_3M$ radical;

d ranges from 1 to 10;

m ranges from 0 to 20;

n ranges from 0 to 500;

o ranges from 0 to 20;

p ranges from 1 to 50;

a ranges from 0 to 50;

b ranges from 0 to 50;

a+b is greater than or equal to 1;

c ranges from 0 to 4, x ranges from 1 to 100,

Y represents a monovalent inorganic or organic anion, such as halide, for example, chloride or bromide, a sulphate or a carboxylate, for example, acetate, lactate or citrate.

Use is preferably made of oxyalkylenated silicones corresponding to the general formula (I) or (II). More preferably, these formulae contain at least one, and even more preferably all, of the following conditions:

c is equal to 2 or 3;

$R_1$ represents a methyl radical;

$R_5$ represents a hydrogen atom, a methyl radical or an acetyl radical, and even more preferably a hydrogen atom;

a ranges from 1 to 25, and even more preferably from 2 to 15;

b is equal to 0;

n ranges from 0 to 100;

p ranges from 1 to 20.

The most particularly preferred silicones are, for example, those sold under the trade names FLUID DC 193 by the company Dow Corning, SILWET L 77 by the company OSI, and MAZIL 756 by the company Mazer PPG.

The oxyalkylenated silicones are preferably present in the compositions according to the invention in an amount ranging from 0.01 to 10% by weight, and more preferably from 0.2 to 5% by weight, with respect to the total weight of the composition.

The compositions according to the invention preferably exhibit a viscosity greater than 200 mPa·s.

In the context of the present invention, the term "water-insoluble particles" means solid or non-solid entities which do not dissolve in the aqueous media of the composition.

The water-insoluble particles which can optionally be dispersed in the compositions according to the invention are, for example, silicone gums, resins or oils which may or may not be modified, fluorinated compounds, antidandruff agents, vegetable, mineral or synthetic oils, waxes, pearlescent agents, pigments, fatty acid esters, abrasive particles, such as silica, fragrances or water-insoluble polymers.

Of course, the person skilled in the art will take care to choose the possible compound or compounds to be added to the composition according to the invention so that the advantageous properties intrinsically attached to the composition in accordance with the invention are not, or not substantially, detrimentally affected by the envisaged addition.

The detergent compositions according to the invention exhibit a final pH preferably ranging from 3 to 8. This pH more preferably ranges from 4 to 7.5. Adjustment of the pH to the desired value can be carried out conventionally by addition, depending on the circumstances, either of basifying agents or of acidifying agents which are standard and known to be cosmetically acceptable.

The detergent compositions according to the invention can, of course, in addition contain all the adjuvants generally encountered in the field of detergent compositions for the hair and/or for the body, such as, for example, fragrances, preservatives, sequestering agents, acidifying agents, basifying agents, softeners, foam modifiers, dyes, pearlescent agents, moisturising agents, antidandruff or antiseborrhoeic agents, vitamins, silicones, ceramides, sun screening agents or cationic, anionic, non-ionic or amphoteric polymers.

These compositions can be provided in the form of thickened liquids, creams, or gels, and they are suitable mainly for washing the hair and/or the skin.

A further subject of the invention is a process for washing the skin or keratinous fibres, such as the hair, which comprises the application on the skin or keratinous fibres of a composition as defined above, followed by rinsing with water.

Concrete examples illustrating the invention will now be given. In the following, "AM" means active material.

EXAMPLE 1

A shampoo in accordance with the invention was prepared which had the following composition:

| | |
|---|---|
| Sodium lauryl ether sulphate containing 2.2 mol of ethylene oxide, as an aqueous solution containing 28% of AM | 16.8 g AM |
| Cocoyl betaine, as an aqueous solution containing 30% of AM | 2.7 g AM |
| Oxyethylenated silicone of formula (II) (DC 193 sold by Dow Corning) | 1 g |
| NaCl | 12 g |
| Preservatives, dyes, fragrance | q.s. |
| Water | q.s.p. for 100 g |

The spontaneous pH of the composition was 5.8. The composition exhibited a flow profile with a range of stresses for which the viscosity was constant, followed by a range of stresses for which the viscosity decreased as the stress increased. Observation of the composition with an optical or electron microscope indicated a lamellar structure.

The shampoo was applied on wet hair and a creamy and pleasant foam was rapidly obtained.

A panel of 10 experienced testers compared the foaming power of this composition with that of an identical composition not containing dimethicone copolyol.

The procedure was as follows:

0.75 g of the composition was deposited on a 2.5 g lock of hair. After having washed and rinsed the hands, each tester developed the foam by massaging the lock. 9 testers out of 10 found that the foam of the composition of Example 1 developed faster, was more copious, was less dense and had better behavior than that of the composition not containing dimethicone copolyol.

A composition containing solely water and dimethicone copolyol did not exhibit any foaming power.

EXAMPLE 2

A shampoo in accordance with the invention was prepared which had the following composition:

| | |
|---|---|
| Sodium lauryl ether sulphate containing 2.2 mol of ethylene oxide, as an aqueous solution containing 28% of AM | 14 g AM |
| Cocoylamidopropyl betaine, as an aqueous solution containing 25% of AM (TEGOBETAINE HS from Goldschmidt) | 3 g AM |
| Oxyethylenated silicone of formula (II) in which: | 0.5 g |
| n = 0, $R_1$ = $CH_3$, $R_2$ = $(CH_2)_3O\text{---}(C_2H_4O)_8\text{---}CH_3$ (SILWET L77 from OSI) | |
| Alcohol ($C_{12}$–$C_{15}$) polyoxyethylenated with 2 mol of ethylene oxide | 3 g |
| Polydimethylsiloxane (PDMS) (47 V 500,000 oil from Rhône-Poulenc) | 3 g |
| NaCl | 10 g |
| Preservatives, dyes, fragrance | q.s. |
| HCl | q.s. pH 5 |
| Water | q.s.p. for 100 g |

The composition exhibited a flow profile with a range of stresses for which the viscosity was constant, followed by a range of stresses for which the viscosity decreased as the stress increased. Observation of the composition with an optical or electron microscope indicated a lamellar structure.

This shampoo exhibited good foaming properties and contributed softness and ease of disentangling to the hair.

EXAMPLE 3

A shampoo in accordance with the invention was prepared which had the following composition:

| | |
|---|---|
| Sodium lauryl ether sulphate containing 2.2 mol of ethylene oxide, as an aqueous solution containing 28% of AM | 16.8 g AM |
| Cocoyl betaine | 2.7 g AM |
| Oxyethylenated silicone (FLUID DC 193 sold by Dow Corning) | 0.5 g |
| Alcohol ($C_{12}$–$C_{15}$) polyoxyethylenated with 2 mol of ethylene oxide | 3 g |
| Polydimethylsiloxane (PDMS) (47 V 500,000 oil sold by Rhône-Poulenc) | 3 g |
| NaCl | 10 g |
| Preservatives, dyes, fragrance | q.s. |
| HCl | q.s. pH 5 |
| Water | q.s.p. for 100 g |

The composition exhibited a flow profile with a range of stresses for which the viscosity was constant, followed by a range of stresses for which the viscosity decreased as the stress increased. Observation of the composition with an optical or electron microscope indicated a lamellar structure.

This shampoo exhibited good foaming properties and contributed softness and ease of disentangling to the hair.

EXAMPLE 4

A shampoo in accordance with the invention was prepared which had the following composition:

| | |
|---|---|
| Sodium lauryl ether sulphate containing 2.2 mol of ethylene oxide, as an aqueous solution containing 28% of AM | 16.8 g AM |
| Cocoyl betaine, as an aqueous solution containing 30% of AM | 2.7 g AM |
| Oxyethylenated silicone of formula (II) (DC 193 sold by Dow Corning) | 1 g |
| Manganese acetate | 12 g |
| Preservatives, dyes, fragrance | q.s. |
| Water | q.s.p. for 100 g |

The spontaneous pH of the composition was 5. The composition exhibited a flow profile with a range of stresses for which the viscosity was constant, followed by a range of stresses for which the viscosity decreased as the stress increased. Observation of the composition with an optical or electron microscope indicated a lamellar structure.

The shampoo was applied on wet hair and a creamy and pleasant foam was rapidly obtained.

EXAMPLE 5

A shampoo in accordance with the invention was prepared which had the following composition:

| | |
|---|---|
| Sodium lauryl ether sulphate containing 2.2 mol of ethylene oxide, as an aqueous solution containing 28% of AM | 16.8 g AM |
| Cocoyl betaine, as an aqueous solution containing 30% of AM | 2.7 g AM |
| Oxyethylenated silicone of formula (II) (DC 193 sold by Dow Corning) | 1 g |
| Lithium chloride | 12 g |
| Preservatives, dyes, fragrance | q.s. |
| Water | q.s.p. for 100 g |

The spontaneous pH of the composition was 5. The composition exhibited a flow profile with a range of stresses for which the viscosity was constant, followed by a range of stresses for which the viscosity decreased as the stress increased. Observation of the composition with an optical or electron microscope indicated a lamellar structure.

The shampoo was applied on wet hair and a creamy and pleasant foam was rapidly obtained.

EXAMPLE 6

A shampoo in accordance with the invention was prepared which had the following composition:

| | |
|---|---|
| Sodium lauryl ether sulphate containing 2.2 mol of ethylene oxide, as an aqueous solution containing 28% of AM | 16.8 g AM |
| Cocoyl betaine, as an aqueous solution containing 30% of AM | 2.7 g AM |
| Oxyethylenated silicone of formula (II) (DC 193 sold by Dow Corning) | 1 g |
| Strontium chloride | 12 g |
| Preservatives, dyes, fragrance | q.s. |
| Water | q.s. for 100 g |

The spontaneous pH of the composition is 5. The composition exhibited a flow profile with a range of stresses for which the viscosity was constant, followed by a range of stresses for which the viscosity decreases as the stress increased. Observation of the composition with an optical or electron microscope indicated a lamellar structure.

The shampoo was applied on wet hair and a creamy and pleasant foam was rapidly obtained.

What is claimed is:

1. A detergent cosmetic composition, comprising:
   (a) at least one anionic surfactant in an amount ranging from 5 to 30% by weight;
   (b) at least one nonionic or amphoteric cosurfactant in an amount ranging from 1 to 15% by weight;
   (c) at least one oxyalkylenated silicone in an amount ranging from 0.01 to 10% by weight; and
   (d) at least one electrolyte in an amount ranging from 6 to 20% by weight;

wherein said at least one anionic surfactant, said at least one nonionic or amphoteric cosurfactant, said at least one oxyalkylenated silicone and said at least one electrolyte are present in an amount effective to provide said composition with:
   (i) a rheological flow behavior having a range of stresses for which the viscosity is constant, followed by a range of stresses for which the viscosity decreases as the stress increases, and
   (ii) a lamellar phase structure capable of maintaining in suspension any water-insoluble particles which are present in the composition; and
   wherein said cosurfactant and said anionic surfactant are present in a weight ratio less than or equal to 1.

2. A composition according to claim 1, wherein said at least one anionic surfactant is an alkyl sulphate, alkyl ether sulphate, alkylamido ether sulphate, monoglyceride sulphate, alkyl glyceryl sulphonate, alkyl sulphonate, alkyl phosphate, alkyl amide sulphonate, alkylaryl sulphonate, α-olefin sulphonate, alkyl sulphosuccinate, alkyl ether sulphosuccinate, alkyl amide sulphosuccinate, alkyl sulphosuccinamate, alkyl sulphoacetats, alkyl ether phosphate, acylisethionate, N-acylamino acid, fatty acid salt, alkyl D-galactosiduronic acid or a salt thereof, or a polyoxyalkylenated ether carboxylic acid.

3. A composition according to claim 2, wherein said N-acylamino acid is an N-acylsarcosinate, an N-acylglutamate or an N-acyltaurate.

4. A composition according to claim 2, wherein said fatty acid salt is a salt of undecylenic acid, oleic acid, rinoleic acid, palmitic acid, stearic acid, coconut oil acid, hydrogenated coconut oil acid or acyl hydroxy acid.

5. A composition according to claim 4, wherein said acyl hydroxy acid salt is an acyllactylate.

6. A composition according to claim 2, wherein said ployoxyalkylenated ether carboxylic acid contains from 2 to 24 ethylene oxide groups.

7. A composition according to claim 1, wherein said at least one non-ionic cosurfactant is an ethoxylated, propoxylated or glycerolated fatty acid, alkyl phenol, α-diol or alcohol, each having a fatty chain containing from 8 to 28 carbon atoms; a copolymer of ethylene oxide and of propylene oxide; a condensate of ethylene oxide and of propylene oxide with a fatty alcohol; a polyethoxylated fatty amide; a polyethoxylated amine; a polyglycerolated fatty amide containing from 1 to 5 glycerol groups; a polyglycerolated diglycolamide; an optionally oxyethylenated fatty acid ester of sorbitan; a fatty acid ester of sucrose; a polyoxyalkylenated fatty acid ester; an optionally oxyalkylenated alkylpolyglycoside; an alkyl glucoside ester; an N-alkylglucamine derivative; an N-acylmethylglucamine derivative; an amine oxide or a mixture of any of said compounds.

8. A composition according to claim 7, wherein said ethoxylated fatty acid, alkyl phenol, α-diol or alcohol contains from 1 to 50 ethylene oxide groups.

9. A composition according to claim 7, wherein said propoxylated fatty acid, alkyl phenol, α-diol or alcohol contains from 1 to 50 propylene oxide groups.

10. A composition according to claim 7, wherein said glycerolated fatty acid, alkyl phenol, α-diol or alcohol contains from 1 to 30 glycerol groups.

11. A composition according to claim 7, wherein said polyethoxylated fatty amine and said polyethoxylated fatty amide contain from 2 to 30 moles of ethylene oxide.

12. A composition according to claim 1, wherein said at least one amphoteric cosurfactant is a secondary or tertiary aliphatic amine derivative in which the aliphatic radical is a linear or branched chain containing from 8 to 22 carbon atoms and containing at least one carboxylate, sulphonate, sulphate, phosphate or phosphorate water-solubilizing anionic group.

13. A composition according to claim 12, wherein said at least one amphoteric cosurfactant is an alkyl betaine, alkyl dimethyl betaine, alkyl sulphobetaine, alkylamidoalkyl betaine, alkylamidoalkyl sulphobetaine, imidazoline derivative, or a mixture of any of said compounds.

14. A composition according to claim 13, wherein said imidazoline derivative is an amphocarboxyglycinate derivative or an amphocarboxypropionate derivative.

15. A composition according to claim 1, wherein said at least one electrolyte exhibits a solubility in water ranging from 0.1 to 300 g %.

16. A composition according claim 1, wherein said at least one electrolyte is a metal salt, an amine salt, an ammonium salt or a basic amino acid salt.

17. A composition according to claim 16, wherein said metal salt is an alkali metal salt, an alkaline-earth metal salt, a transition metal salt and or salt of a metal from groups IIIA and IVA of the Periodic Table of the Elements.

18. A composition according to claim 16, wherein said metal salt is a lithium, magnesium, strontium, barium, yttrium, neodymium, gadolinium, manganese or zinc salt.

19. A composition according to claim 18, wherein said metal salt is a magnesium or strontium salt.

20. A composition according to claim 16, wherein said metal salt is a carbonate, bicarbonate, sulphate, glycerophosphate, borate, chloride, nitrate, acetate, hydroxide, persulphate, α-hydroxy acid salt, amino acid salt or fatty acid salt.

21. A composition according to claim 20, wherein said at least one electrolyte is strontium chloride or nitrate.

22. A composition according to claim 1, wherein said at least one oxyalkylenated silicone is a compound of formula (I), (II), (III), (IV) or (V):

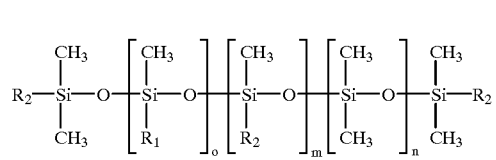

(I)

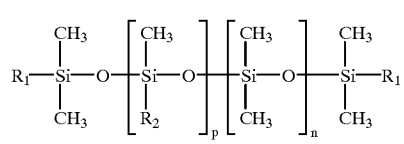

(II)

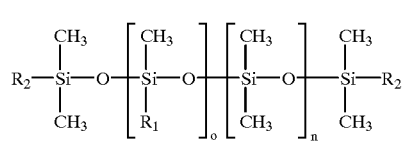

(III)

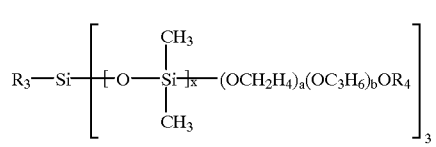

(IV)

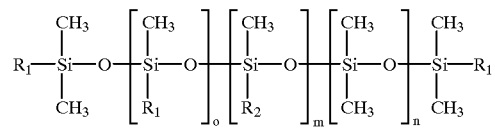

(V)

wherein:
$R_1$, which is identical or different, represents a linear or branched $C_{1-C30}$ alkyl radical or a phenyl radical;

$R_2$, which is identical or different, represents $-C_cH_{2c}-O-(-C_2H_4O)_a(-C_3H_6O)_b-R_5$ or $-C_cH_{2c}-O-(-C_4H_8O)_a-O-R_5$;

$R_3$ and $R_4$, which are identical or different, represent a linear or branched $C_1-C_{12}$ alkyl radical;

$R_5$, which is identical or different, represents a hydrogen atom, a linear or branched alkyl radical containing from 1 to 12 carbon atoms, a linear or branched alkoxy radical containing from 1 to 6 carbon atoms, a linear or branched acyl radical containing from 2 to 12 carbon atoms, a hydroxyl radical, $-SO_3M$, $-OCOR_6$, a $C_1-C_6$ aminoalkoxy optionally substituted on the amine, a $C_2-C_6$ aminoacyl optionally substituted on the amine, $-NHCH_2CH_2COOM$, $N(CH_2CH_2COOM)_2$, an amino alkyl optionally substituted on the amine and on the alkyl chain, a $C_1-C_{30}$ carboxyacyl, a phosphono group optionally substituted by one or two substituted amino alkyl radicals, $-CO(CH_2)_dCOOM$, $-OCOCHR_7(CH_2)_dCOOM$, $-NHCO(CH_2)_dOH$ or $-NH_3Y$;

M, which is identical or different, represents a hydrogen atom, Na, K, Li, $NH_4$ or an organic amine;

$R_6$ represents a linear or branched $C_1-C_{30}$ alkyl radical;

$R_7$ represents a hydrogen atom or an $SO_3M$ radical;

d ranges from 1 to 10;

m ranges from 0 to 20;

n ranges from 0 to 500;

o ranges from 0 to 20;

p ranges from 1 to 50;

a ranges from 0 to 50;

b ranges from 0 to 50;

a+b is greater than or equal to 1;

c ranges from 0 to 4;

x ranges from 1 to 100; and

Y represents a monovalent inorganic or organic anion.

23. A composition according to claim 22, wherein each of $R_3$ and $R_4$ is a methyl radical.

24. A composition according to claim 22, wherein said at least one oxyalkylenated silicone has the formula (I) or (II) and satisfies at least one of the following conditions:

c is equal to 2 or 3, $R_1$ represents a methyl radical, $R_5$, which is identical or different, represents a hydrogen atom, a methyl radical or an acetyl radical, a ranges from 1 to 25, b is equal to 0, n ranges from 0 to 100, and p ranges from 1 to 20.

25. A composition according to claim 24, wherein $R_5$ is hydrogen.

26. A composition according to claim 24, wherein a ranges from 2 to 15.

27. A composition according to claim 1, wherein said at least one oxyalkylenated silicone is present in an amount ranging from 0.01 to 10% by weight, with respect to the total weight of the composition.

28. A composition according to claim 27, wherein said at least one oxyalkylated silicone is present in an amount ranging from 0.2 to 5% by weight with respect to the total weight of the composition.

29. A process for cleaning the skin or keratinous fibres, said process comprising the steps of applying to said skin or keratinous fibres an effective amount of at least one composition according to claim 1 and then rinsing said skin or kertanious fibres.

30. A process according to claim 29, wherein said keratinous fibre is hair.

31. A process for washing the skin or keratinous fibres, said process comprising the steps of applying to said skin or keratinous fibres an effective amount of at least one composition according to claim 1 and then rinsing said skin or kertanious fibres.

32. A process according to claim 31, wherein said keratinous fibre is hair.

* * * * *

UNITED STATES PATENT AND TRADEMARK OFFICE
CERTIFICATE OF CORRECTION

PATENT NO. : 6,074,633      Page 1 of 1
DATED : June 13, 2000
INVENTOR(S) : Dubief et al.

It is certified that error appears in the above-identified patent and that said Letters Patent is hereby corrected as shown below:

Please correct the following errors:

Column 10,
Line 36, change "ployoxyalkylenated" to -- polyoxyalkylenated --.
Line 49, change "alkylpolyg" to -- alkylpoly --; and
Line 50, change "lycoside" to --glycoside --.

Column 12,
Line 12, change "$C_{1-C30}$" to $C_1$-$C_{30}$ --.

Signed and Sealed this

Fourteenth Day of August, 2001

Attest:

NICHOLAS P. GODICI
Attesting Officer     Acting Director of the United States Patent and Trademark Office